United States Patent [19]

Koppel et al.

[11] 4,158,004
[45] Jun. 12, 1979

[54] PROCESS FOR ANTIBIOTIC FR 1923 AND RELATED COMPOUNDS

[75] Inventors: Gary A. Koppel; Robin D. G. Cooper, both of Indianapolis, Ind.

[73] Assignee: Eli Lilly and Company, Indianapolis, Ind.

[21] Appl. No.: 739,161

[22] Filed: Nov. 5, 1976

[51] Int. Cl.$^2$ .................. C07D 201/08; C07D 205/08
[52] U.S. Cl. ........................... 260/239 A; 260/307 F; 260/306.7 C
[58] Field of Search ..................................... 260/239 A

[56] References Cited

U.S. PATENT DOCUMENTS 3,991,069  11/1976  Barton et al. .................... 260/239 A

FOREIGN PATENT DOCUMENTS 2615621  10/1976  Fed. Rep. of Germany.

OTHER PUBLICATIONS

Baldwin et al., I, J. Amer. Chem. Soc. 97, 5957–5958 (1975).
Baldwin et al. II, J. Amer. Chem. Soc. 98, 3045 (1976).
Fujisawa, Derwent 06757X104 . NL7508–008.
Fujisawa, Derwent 11208X107 B03.

Primary Examiner—Donald G. Daus
Assistant Examiner—Mark L. Berch
Attorney, Agent, or Firm—William B. Scanlon; Arthur R. Whale

[57] ABSTRACT

Process for 1-[α-(carboxy)-4-hydroxy or protected-hydroxybenzyl]-3-acylamidoazetidin-2-one esters, useful intermediates for preparing antibiotic FR 1923, comprising the ring opening of a 2-acyl-3,3-dialkyl-7-oxo-α-[4-(protected-hydroxyphenyl]-4-thia-2,6-diazabicyclo[3.2.0]heptane-6-acetic acid, ester sulfoxide with a sulfonic acid and heat to provide a 3-acylamido-4-(2-oxaalkylthio)azetidin-2-one ester which on treatment with sulfuryl chloride affords a reaction product mixture that is then reduced with an organo tin hydride, e.g., tri(n-butyl)tin hydride, to the product. N-Deacylation of the 3-acylamido group followed by acylation with the 3-acyl portion of FR 1923, deblocking of the amino-protecting group and deesterification affords FR 1923.

9 Claims, No Drawings

PROCESS FOR ANTIBIOTIC FR 1923 AND RELATED COMPOUNDS

BACKGROUND OF THE INVENTION

This invention relates to the total synthesis of the β-lactam antibiotic FR 1923 and related compounds. This antibiotic has been previously described in Belgian Pat. No. 830,934 and its isolation and characterization has been described by H. Aoki, et al., 15th *Interscience Conference on Antimicrobial Agents and Chemotherapy*, Abstract No. 97, September, 1975. The antibiotic has the following strucural formula.

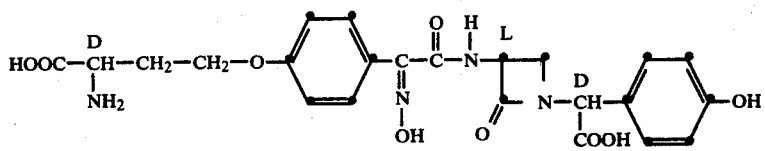

Antibiotic FR 1923 has been obtained by culturing *Nocardia uniformis* var. *Tsuyamanensis* ATCC 21806 as described by U.S. Pat. No. 3,923,977 issued Dec. 2, 1975.

This invention relates to a process for the synthesis of antibiotic FR 1923. In particular, this invention relates to a chemical process for the preparation of the "nucleus" of antibiotic FR 1923. The nucleus is represented by the following structural formula:

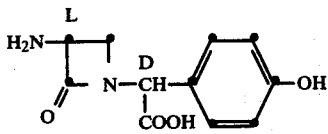

This invention also relates to certain derivatives of FR 1923 and to the intermediates useful in the synthesis thereof.

DETAILED DESCRIPTION OF THE INVENTION

The antibiotic FR 1923 of the foregoing structural formula is characterized as a 2-azetidinone substituted in the 1-position with an α-carboxy-4-hydroxybenzyl group having the D-configuration and in the 3-position by a 2-[4-(3-amino-3-carboxypropoxy)phenyl]-2-hydroxyiminoacetamido group. In the latter group the carbon bearing the amino and carboxy groups has the D-configuration while the hydroxyimino (oxime) group can have either the syn or anti configuration, preferably the syn configuration.

This invention provides a process for the preparation of FR 1923, the nucleus thereof, related compounds and intermediates useful in the preparation thereof.

The process of this invention comprises the stereochemical synthesis of the nucleus of antibiotic FR 1923, D-1-(α-carboxy-4-hydroxybenzyl)-3β-aminoazetidin-2-one, and the acylation thereof with an amino-protected and esterified derivative of 4-(3-amino-3-carboxypropoxy)phenylglyoxylic acid or the oxime derivative thereof. The preparation of the phenylglyoxylic acid derivative and the oxime thereof is described in co-pending application Ser. No. 739,160 filed this even data, now abandoned.

According to the process of this invention, a 2,2-dialkyl-3-acylthiazolidine-4-carboxylic acid having the L-configuration is reacted with an ester of a 4-protected-hydroxy-D-phenylglycine to obtain the corresponding amide (1) as shown in the following reaction scheme.

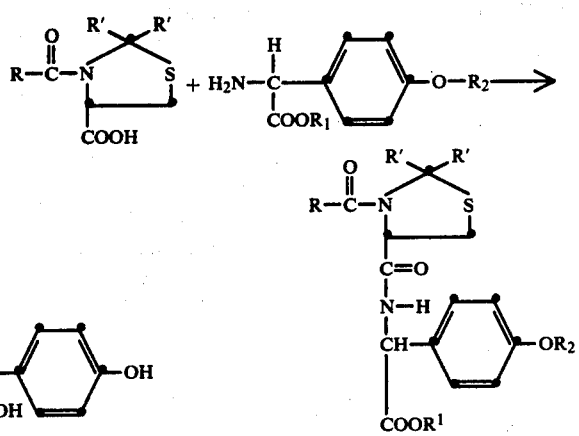

In the above formula, R is phenyl, $C_1-C_3$ alkyl, or benzyl; R' is methyl or ethyl; $R_1$ is methyl, benzyl, 4-methoxybenzyl, 2,2,2-trichloroethyl, or diphenylmethyl; and $R_2$ is benzyl, diphenylmethyl, or 4-methoxybenzyl.

The 2,2-dialkyl-3-acylthiazolidine-4-carboxylic acids employed in the preparation of the above amides (1) are prepared by reacting L-cysteine with either acetone or diethylketone to obtain, respectively, the 2,2-dimethyl and 2,2-diethylthiazolidine-4-carboxylic acid. The reaction is carried out by heating the amino acid with the desired ketone at the reflux temperature. The ketone is best used as the solvent in the reaction. After the reaction is complete the mixture is concentrated by evaporation to remove excess ketone and the thiazolidine-4-carboxylic acid precipitates from the concentrate on cooling.

The 2,2-dimethyl (or diethyl) thiazolidine carboxylic acid is then acylated with the acyl chloride

to provide the corresponding 3-acyl derivative. The acylation is preferably carried out in dry acetone with the stoichiometric amount of the acyl halide in the presence of a hydrogen halide acceptor. Preferred hydrogen halide acceptors are the alkylene oxides such as propylene oxide or butylene oxide.

Illustrative of the acyl chlorides which are used to acylate the thiazolidine carboxylic acid are benzoyl chloride, phenylacetyl chloride, and acetyl chloride.

The preparation of the amide (1) is carried out by reacting the active ester of the thiazolidine-4-carboxylic acid, formed with 1-hydroxybenzotriazole, with the esterified and protected-hydroxy-phenylglycine in the presence of dicyclohexylcarbodiimide.

The thiazolidine amide (1) is converted to the cyclic thiazolidine azetidinone represented by the Formula 4 as shown in the following reaction scheme.

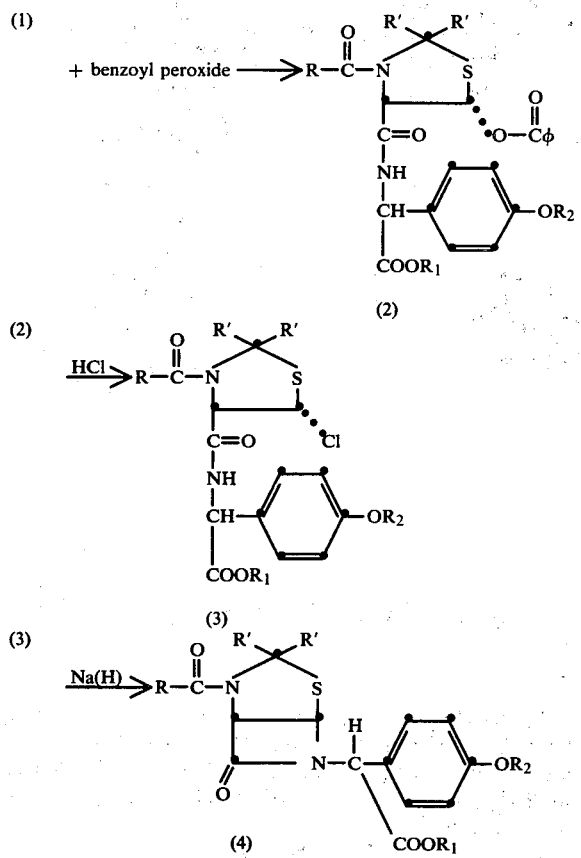

As shown above, the thiazolidine amide (4) is first converted to the 5α-benzoate derivative (2) by reacting (1) with benzoyl peroxide. The reaction is carried out by heating the amide in an inert solvent with benzoyl peroxide. Suitable solvents include the hydrocarbon solvents such as benzene and toluene, or the chlorinated hydrocarbon solvents such as methylene chloride and chloroform. An excess of benzoyl peroxide is employed and preferably between about a 2 and 4 molar excess.

The 5α-benzoate (2), which can be purified and separated from unreacted starting material by chromatography over silica gel, is then reacted with hydrogen chloride in an inert solvent at a temperature between about −20° and about 5° C. to form the corresponding 5α-chloro thiazolidine amide represented by the above Formula (3). The reaction is conveniently carried out in a chlorinated hydrocarbon solvent such as methylene chloride or chloroform, and the progress of the reaction can be followed by thin layer chromatography.

The 5α-chloro compound (3) on treatment under anhydrous conditions with a strong base such as sodium hydride or 1,5-diazabicyclo[5.4.0]undec-5-ene (DBU) undergoes cyclization to form the bicyclic thiazolidine azetidinone represented by the above Formula (4).

The cyclization to form (4) is carried out at a temperature between about 0° and 30° C. in an inert solvent. Suitable solvents include those previously mentioned in connection with the foregoing reactions, for example, the halogenated hydrocarbon solvents such as chloroform, DMF and methylene chloride, and trichloroethane. The product (4) of the cyclization is best purified for use in succeeding reactions in this process by chromatography over silica gel. Gradient elution employing a gradient of benzene to benzeneethyl acetate (7:3, v:v) is a suitable chromatographic system for the purification of compound 4.

During the cyclization reaction as described above, the asymmetric center, originally having the D-configuration, (via formation of the amide with the D-phenylglycine) undergoes some inversion to the L-configuration. The desired D-isomer can be separated from the L-isomer by fractional crystallization. For example, a solution of the mixture of isomers in ethyl acetate on cooling and standing first deposits crystals of the less soluble D-isomer and the filtrate on dilution with petroleum ether affords a crystalline precipitate of the L-isomer.

Alternatively, it has been discovered that compound 4 undergoes isomerization in wet pyridine from which the D-isomer can be crystallized. Accordingly, the cyclization product, compound 4, which is a mixture of the D- and L-isomers is dissolved in wet pyridine at about room temperature and on standing the D-isomer precipitates.

For convenience, the compound 4 is referred to herein as a thiazolidine azetidinone derivative. The compounds represented by the Formula 4 are formally named 2-acyl-3,3-dialkyl-7-oxo-α-[4-(protected-hydroxy)phenyl]-4-thia-2,6-diazabicyclo[3.2.0]heptane-6-acetic acid esters.

The thiazolidine azetidinone having the D-configuration is oxidized with a peracid to the corresponding sulfoxide and the latter, via an acid catalyzed rearrangement, affords the ring-opened substituted azetidinone represented by the Formula 6 in the following reaction scheme.

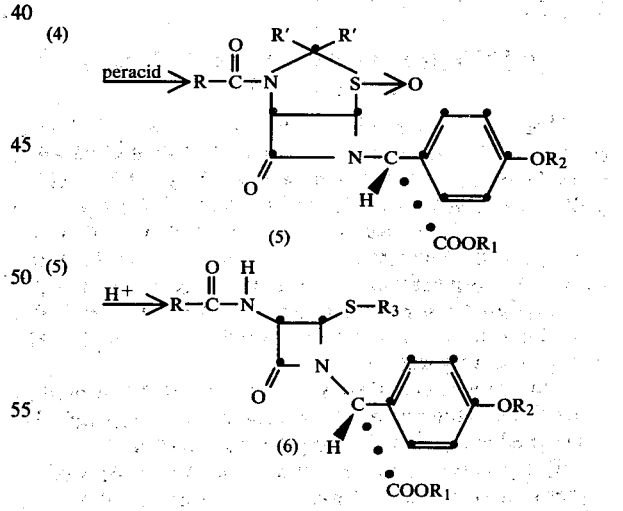

In the above reaction scheme, the terms R, R', R$_1$, and R$_2$ have the previously defined meanings and the term R$_3$ represents either a 2-oxapropyl group of the formula (a) or a 2-oxapentyl group represented by the Formula (b) below:

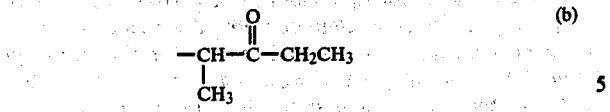

The thiazolidine azetidinone (4) is reacted with a peracid in an inert solvent to provide the corresponding sulfoxide (5). Peracids which are suitable for the oxidation include peracids such as peracetic acid, perbenzoic acid, perphthalic acid, m-chloroperbenzoic acid, and like organic peracids. The reaction is best carried out in the cold, for example, at a temperature between about 0° C. and about 15° C. An excess of the peracid is best employed. The reaction is carried out in a nonoxidizable solvent and the chlorinated hydrocarbon solvents such as methylene chloride and trichloro or tetrachloroethane are suitable.

The sulfoxide obtained in the above-described oxidation is then heated at a temperature between about 80° and about 120° C. in a highly polar aprotic solvent such as dimethylacetamide or dimethylformamide in the presence of an acid catalyst and water to effect the rearrangement and provide a compound represented by the Fromula 6. Acid catalysts which can be employed in the rearrangement include the lower alkyl or aryl sulfonic acids such as methanesulfonic acid, ethanesulfonic acid, benzenesulfonic acid, p-chlorobenzenesulfonic acid, and p-toluenesulfonic acid. The reaction is best carried out in a highly polar aprotic solvent, for example dimethylacetamide with a co-solvent such as an aromatic hydrocarbon solvent, for example benzene, toluene or xylene, at the reflux temperature. The reaction can be followed by thin layer chromatography and when incomplete, the starting material can be separated from the rearrangement product (6) by chromatography.

When R' in the sulfoxide starting material (5) represents ethyl, the term $R_3$ in the rearrangement product (6) is represented by the 2-oxopentyl group (b) as shown above. When R' in the sulfoxide represents methyl, then $R_3$ in the rearrangement product is represented by the 2-oxopropyl group (a) as shown above.

The compounds represented by the formula 6 are formally named as esters as 1-azetidineacetic acid. For example, the compound represented by the formula 6 wherein R is phenyl, $R_1$ and $R_2$ are both benzyl, and $R_3$ is the 2-oxypropyl group, represented by the formula (a) above, is named 3-(benzoylamino)-2-oxo-4-[(2-oxopropyl)-thio]-α-[4-(benzyloxy)phenyl]-1-azetidineacetic acid, benzyl ester.

In the next stage of the process the compound represented by the formula 6 above is reacted in an inert solvent at a temperature between −25° and about 10° C. with excess sulfuryl chloride to effect displacement of the 4-(2-oxoalkylthio) group represented by -$SR_3$ to obtain the 4-chloro substituted azetidinone. It appears, however, that under the acidic conditions of the displacement reaction the 4-chloro substituent is itself displaced to some extent by an intramolecular cyclization reaction involving the carbonyl function of the 3-acyl moiety to form an oxazoline azetidinone represented by the following formula.

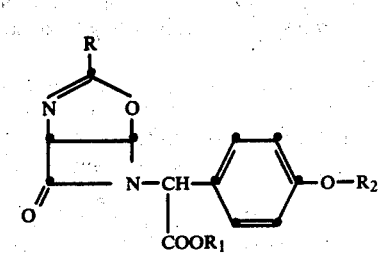

The nuclear magnetic resonance spectrum of the reaction product mixture tends to support a mixture comprising both the oxazoline azetidinone represented by the above formula and the desired 4-chloro azetidinone represented by the following formula.

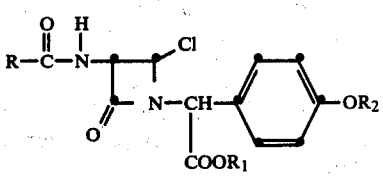

However, the spectral evidence obtained on the reaction product mixture is insufficient to conclude the exact nature of the reaction product mixture.

The reaction product mixture obtained above is subjected to reduction with a trialkyl or triaryltin hydride or a mixed alkylaryltin hydride represented by the following formula

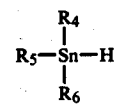

wherein $R_4$, $R_5$, and $R_6$ independently are $C_1$-$C_4$ alkyl, phenyl, or phenyl substituted by methyl or chloro.

The reaction is carried out by employing an excess of the tin hydride for example, about a 2 molar excess in the presence of an equivalent amount of azobisisobutyronitrile. The reaction is carried out in an inert aromatic hydrocarbon solvent such as benzene, toluene, or one of the xylenes. The reaction is performed preferably in an inert atmosphere such as nitrogen or argon by heating the reaction mixture at a temperature between about 65° and about 95° C. The tin hydride reduction product is represented by the formula 7

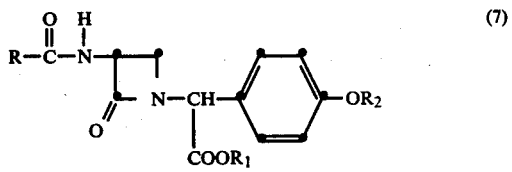

wherein R, $R_1$ and $R_2$ have the same meanings as previously defined herein.

Representative of the tin hydrides of the above formula are tri(n-butyl)tin hydride, tri(n-propyl)tin hydride, trimethyltin hydride, triphenyltin hydride, tri(p-tolyl)tin hydride, and the mixed alkyl aryltin hydride such as di(n-butyl)phenyltin hydride, dimethylethyltin hydride, and diphenylmethyltin hydride.

The preferred tin hydride of this invention is tri(n-butyl)tin hydride and the preferred solvent in the reaction is toluene.

The 3-acylamidoazetidin-2-one (7) reduction product is recovered from the reaction mixture by evaporating the mixture to obtain a dry crude residue of the product which is best purified by chromatography over silica gel.

In the above formula 7, R, $R_1$, and $R_2$ have the same meanings as previously defined herein. The 3-acylamino group has the $\beta$-configuration, while the 1-substituent group having the asymetric center has the D-configuration. Illustrative of the compounds represented by the formula 7 are 1-[α-(benzyloxycarbonyl)-4-benzyloxybenzyl]-3-benzamidoazetidin-2-one, 1-[α-(p-methoxybenzyloxycarbonyl)-4-p-methoxybenzyloxybenzyl]-3-acetamidoazetidin-2-one, and like esters wherein $R_1$ is p-methoxybenzyl, 2,2,2-trichloroethyl, or diphenylmethyl, and wherein $R_2$ is benzyl, diphenylmethyl or 4-methoxybenzyl.

The above product is N-deacylated to provide the corresponding 3$\beta$-aminoazetidin-2-one represented by the following structural formula

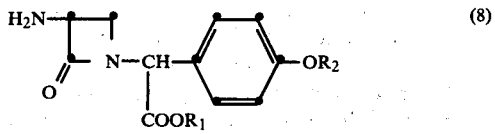

wherein $R_1$ and $R_2$ have the meanings previously defined herein.

The 3-aminoazetidin-2-one represented by the above formula (8) is an esterified and hydroxy-protected FR 1923 nucleus. The nucleus (8) is then acylated with an amino-protected ester of 4-(D-3-amino-3-carboxypropoxy)phenylglyoxylic acid to provide the keto precursor of the antibiotic FR 1923, wherein the amino, hydroxy, and carboxy groups are protected. The acylation is illustrated in the following reaction scheme The acylation of (8) to form the FR 1923 precursor can be carried out by coupling the glyoxylic acid with the free 3$\beta$-amino nucleus compound with a condensing agent such as a carbodiimide or by forming a mixed anhydride of the glyoxylic acid and reacting the anhydride with the 3$\beta$-amino nucleus in the presence of triethylamine.

The preferred acylation method is the former wherein the glyoxylic acid is condensed with the amine nucleus with the aid of a condensing agent. For example, the 3$\beta$-amino nucleus as an ester (8) is reacted in an inert solvent such as methylene chloride or tetrahydrofuran with the amino-protected and carboxy-protected phenylglyoxylic acid (9) in the presence of an equimolecular amount or a small excess of a carbodiimide such as dicyclohexylcarbodiimide. The reaction mixture is maintained substantially anhydrous for best results. The reaction is carried out with stirring at about room temperature. After the reaction is complete the insoluble dicyclohexylurea is filtered and the acylation product (10) is recovered from the filtrate.

As mentioned above, the acylation can also be carried out with a mixed anhydride of the phenylglyoxylic acid (9). Suitable mixed anhydrides can be prepared with methyl chloroformate or isobutyl chloroformate. The acylation of the amino nucleus ester (8) is carried out at about 5° to about 25° C. with stirring in a suitable solvent such as methylene chloride or tetrahydrofuran in the presence of a tertiary amine preferably triethylamine. The reaction is carried out under substantially anhydrous conditions.

The acylation product (10) is next converted to the oxime via the reaction with hydroxylamine hydrochloride in an inert aqueous solvent in the presence of a hydrogen halide acceptor to provide the esterified and amino-protected FR 1923. Following the formation of the oxime, the ester groups R' and $R_1$, the amino-protecting group R" and the hydroxyl-protecting group $R_2$ are removed to provide the antibiotic FR 1923.

Alternatively, the 3-amino nucleus compound (8) can be acylated with an esterified and amino-protected 4-

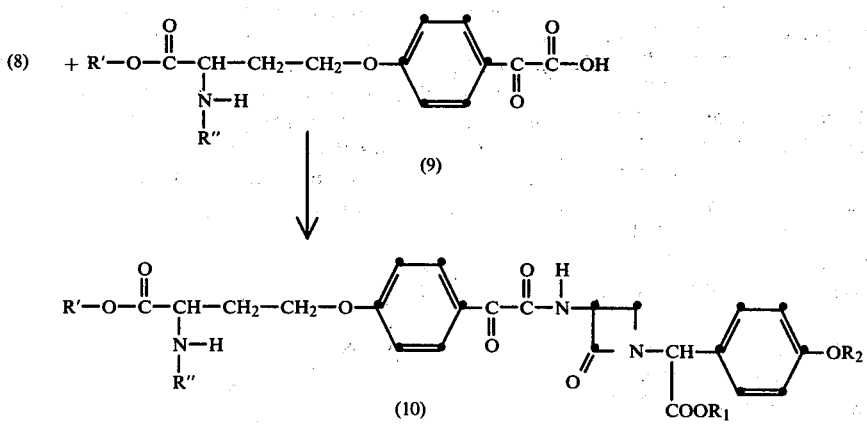

wherein R' represents a carboxylic acid-protecting group which is readily removable under acidic conditions for example, R' represents diphenylmethyl, benzyl, 4-methoxybenzyl, 2,4,6-trimethylbenzyl, or phthalimidomethyl; R" represents an amino-protecting group for example, the t-butyloxycarbonyl group and $R_1$ and $R_2$ have the same meanings as previously defined herein.

(D-3-amino-3-carboxypropoxy)phenylglyoxylic acid oxime in which the oximino group is protected with acetyl or chloroacetyl.

The amino-protected and esterified phenylglyoxylic acid (9) is prepared by the method described in co-pending application serial No. 739,160 now abandoned, filed this even date. As described therein an amino-protected salt of D-methionine of the formula

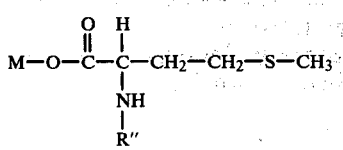

for example the salt wherein M is dicyclohexylammonium and R″ is as previously defined herein, is converted to the trimethylsilyl ester and is alkylated on the sulfur atom with an alkyl or benzyl iodide, for example methyl iodide and the alkylsulfonium iodide of the formula

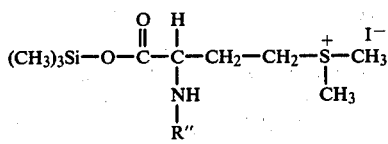

is reacted in an inert solvent with potassium t-butoxide to form the cyclic amino-protected D-homoserine lactone of the formula

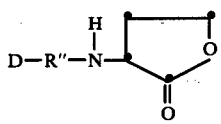

The lactone is hydrolyzed with an alkali metal hydroxide to the amino-protected D-homoserine alkali metal salt of the formula

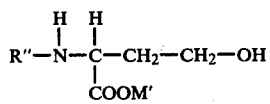

wherein M′ is sodium or potassium, and the latter is esterified e.g., with diphenylmethyl bromide. The esterified D-homoserine is then coupled with a 4-hydroxyphenylglyoxylic acid ester for example, the p-nitrobenzyl ester with a trialkyl or triarylphosphine, and preferably triphenylphosphine, and diethyl azodicarboxylate to the amino-protected diester of the formula

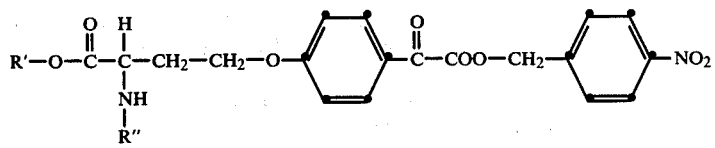

The p-nitrobenzyl ester group is selectively de-esterified by reduction whereby the other ester R′, which is selected from among the acid-labile ester groups, remains substantially intact. For example, the p-nitrobenzyl ester group is removed via reduction with sodium sulfide while the ester group R′ which is an acid sensitive group such as the diphenylmethyl group remains unaffected under the reduction conditions. The selective de-esterification product, the phenylglyoxylic acid, is represented by the formula

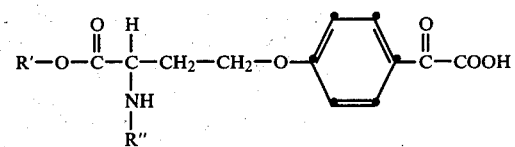

As was previously mentioned, the product of the process of this invention represented by the formula (7) is N-deacylated to provide the esterified and hydroxy-protected derivative of the nucleus of FR 1923 (8). The N-deacylation is carried out by following the known procedures used in the N-deacylation of 7-acylamidocephalosporin compounds. For example, the compound of the formula (7) wherein R, $R_1$ and $R_2$ have the same meanings as previously defined herein is reacted at a temperature of about 0° to 65° C. in anhydrous benzene with an excess of phosphorus pentachloride in the presence of pyridine to form, in solution, the imino chloride of the 3-acylamido group. The imino chloride is treated with methyl alcohol to convert the imino chloride to the corresponding imino ether and the latter is hydrolyzed with water to provide the 3-amino nucleus compound.

According to one aspect of this invention, there is provided a process for the preparation of the 3β-acylamido azetidin-2-one compounds represented by the above formula (7). These compounds are useful intermediates in the preparation of the antibiotic FR 1923 as described herein.

Illustrative of the compounds produced by the process of this invention are:

1-[α-(benzyloxycarbonyl)-4-benzyloxybenzyl]-3-benzamidoazetidin-2-one,

1-[α-(diphenylmethyloxycarbonyl)-4-benzyloxybenzyl]-3-acetamidoazetidin-2-one,

1-[α-(benzyloxycarbonyl)-4-benzyloxybenzyl]-3-phenylacetamidoazetidin-2-one, and 1-[α-(4-methoxybenzyloxycarbonyl)-4-benzyloxybenzyl]-3-benzamidoazetidin-2-one.

In a preferred embodiment of the process of this invention, 3-benzoyl-2,2-dimethyl-4-thiazolidinecarboxylic acid is converted to the active ester formed with 1-hydroxybenzotriazole and the latter condensed with benzyl D-4-benzyloxyphenylglycinate with the condensing agent dicyclohexylcarbodiimide to form the amide N-[α-(benzyl D-4-benzyloxyphenylacetate)]-3-benzoyl-2,2-dimethyl-4-thiazolidinecarboxamide (formula 1; R=phenyl, R′=CH₃, $R_1$ and $R_2$=benzyl); the amide is reacted in benzene with excess benzoyl peroxide to form the corresponding carboxamide 5α-benzoate, N-[α-(benzyl D-4-benzyloxyphenylacetate)]-3-benzoyl-2,2-dimethyl-4-thiazolidinecarboxamide-5-benzoate. The benzoate is reacted in dry methylene chloride at a temperature of about 0° C. with hydrogen chloride to form the corresponding 5α-chloro compound, N-[α-(benzyl D-4-benzyloxyphenylacetate)]-3-benzoyl-2,2-dimethyl-5α-chloro-4-thiazolidinecarboxamide and the 5-chloro compound is reacted under anhydrous conditions in methylene chloride and DMF with sodium hydride to effect the intramolecular cyclization and form the thiazolidine azetidinone formally named as 2-benzoyl-3,3-dimethyl-7-oxo-α-[4-(benzyloxy)phenyl]-4-thia-2,6-diazobicyclo[3.2.0]heptane-6-acetic acid, benzyl ester (formula 4; R=phenyl, R'=methyl, $R_1$ and $R_2$=benzyl). The thiazolidine azetidinone is reacted in an inert solvent at about 0° C. with m-chloroperbenzoic acid to form the corresponding sulfoxide which on treatment in a mixture of dimethylacetamide and benzene with methanesulfonic acid at the reflux temperature affords via ring opening, 3-benzamido-2-oxo-4-[(2-oxopropyl)thio]-α-[4-(benzyloxy)phenyl]-1-azetidineacetic acid benzyl ester (formula 6; R=phenyl, $R_3$=2-oxapropyl, $R_1$ and $R_2$=benzyl). The thioketone benzyl ester ring opened product is reacted with sulfuryl chloride at a temperature of about 0° C., the reaction product mixture is isolated and is reacted in toluene with tri(n-butyl)tin hydride in the presence of azobisisobutyronitrile to provide the product of the process 1-[α-(benzyloxycarbonyl)-4-benzyloxybenzyl]-3-benzamidoazetidinone-2 (formula 7; R=phenyl, $R_1$ and $R_2$=benzyl).

As previously described, during the cyclization of the 5-chlorothiazolidine amide with base to form the thiazolidine azetidinone some epimerization of the asymetric center occurs to form a mixture of the D- and L-isomers. It is preferable to carry out the remaining steps in the process on intermediates having the D-configuration. Accordingly, the thiazolidine azetidinone is fractionally recrystallized to obtain the D-isomer or alternatively and as previously described the mixture of isomers is dissolved in a minimum amount of wet pyridine at room temperature and the selectively precipitated D-isomer is collected by filtration.

The epimerized thiazolidine azetidinone can be used in the process and the product represented by the above formula (7) obtained as a mixture of the D- and L-isomers. Following the N-deacylation reaction and acylation with the amino-protected and esterified FR 1923 side chain as described previously, the antibiotic FR 1923 is obtained as a mixture of the D- and L-isomers.

In performing the process of this invention, certain starting materials and intermediates are preferred. For example, in the above formulas, R is preferably phenyl, R' is methyl, and $R_1$ and $R_2$ are preferably benzyl.

In a further aspect of this invention certain novel compounds are provided which are useful intermediates in the preparation of the antibiotic FR 1923. These intermediates are represented by the following formula

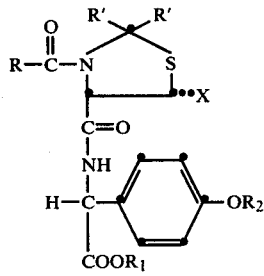

wherein R, $R_1$, $R_2$, and R' have the same meanings as previously defined herein and X is chloro or benzoyloxy, said X-substituent having the α-configuration. Preferred compounds of the above formula are those having the D-configuration. Further preferred are compounds of the above formula wherein R is phenyl, R' is methyl, and $R_2$ is benzyl.

A further group of novel intermediates is represented by the following formula,

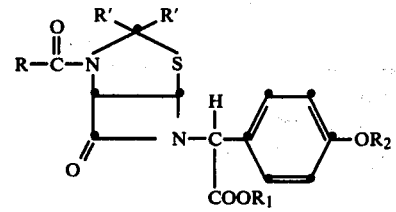

wherein R, $R_1$, $R_2$, and R' have the same meanings as previously defined herein. Preferred compounds of the above formula are those having the D-configuration. Further preferred compounds of the above formula are represented when R is phenyl, R' is methyl, and $R_2$ is benzyl.

Another group of novel intermediates are represented by the following formula.

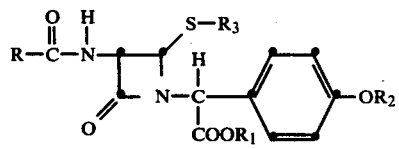

wherein R, $R_1$, and $R_2$ have the same meanings as defined hereinbefore and $R_3$ is a 2-oxopropyl group of the formula

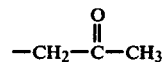

or a 2-oxapentyl group of the formula

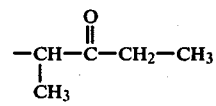

Preferred compounds of the invention of the above formula are represented when R is phenyl and $R_1$ and $R_2$ are benzyl. A further preferred intermediate is represented when R is phenyl, $R_1$ and $R_2$ are benzyl, and $R_3$ is the 2-oxapropyl group. The D-configuration is preferred.

This invention is further exemplified by the following particular examples.

EXAMPLE 1

Preparation of 3-benzoyl-2,2-dimethyl-4-thiazolidinecarboxylic acid

A slurry of 100 g. of L-cysteine in 2 l. of dry acetone was heated at the reflux temperature for about 17 hours. After the reaction mixture was allowed to cool to about 30° C. the unreacted cysteine was filtered and the reaction product, 2,2-dimethyl-4-thiazolidinecarboxylic acid, crystallized from the filtrate. Three crops of the product were obtained via successive filtrations. The combined weight of product was 83 g.

To a suspension of 16 g. (100 mM) of the product in 300 ml. of dry acetone were added 21 ml. of propylene oxide. Next, 11.6 ml. (100 mM) of benzoyl chloride were added dropwise with vigorous stirring. The temperature of the reaction mixture slowly increased from about 25° C. to about 33° C. After an hour all of the thiazolidine had dissolved and the reaction solution began to cool. When the temperature had dropped to 30° C. the reaction solution was evaporated to yield a white solid residue. The solid was dissolved in acetone and was diluted with hexane to crystallize the product. The product, 3-benzoyl-2,2-dimethyl-4-thiazolidinecarboxylic acid, was filtered and dried. The dried product weighed 18.7 g.

EXAMPLE 2

To a solution of 48 g. (181 mmole) of 3-benzoyl-2,2-dimethyl-4-thiazolidinecarboxylic acid, prepared by the procedure described by Example 1, in 1.5 l. of tetrahydrofuran were added 27.8 g. (181 mmole) of 1-hydroxybenzotriazole followed by 37.4 g. (181 mmole) of dicyclohexylcarbodiimide. The mixture was stirred for 30 minutes at room temperature. The reaction mixture developed into a thick slurry resulting from the precipitation of dicyclohexylurea. To the heavy slurry was added 63 g. (181 mmole) of benzyl D-4-benzyloxyphenylglycinate and the reaction mixture was stirred at room temperature for about 2 hours. The reaction mixture was filtered to remove the dicyclohexylurea, the filtrate evaporated under reduced pressure, and the residue was dissolved in ethyl acetate. The solution was washed successively with 5% hydrochloric acid, water, aqueous sodium bicarbonate, and finally with water. The washed solution was dried, treated with carbon, and evaporated to dryness under reduced pressure to yield 107 g. (99% yield) of N-[α-(benzyl D-4-benzyloxyphenylacetate]-3-benzoyl-2,2-dimethyl-4-thiazolidinecarboxamide.

The above thiazolidinecarboxamide ester (107 g.; 0.18 mole) was dissolved in 4 l. of benzene and 175 g. (0.72 mole) of benzoyl-peroxide were added to the solution. The solution was then heated at the reflux temperature for 4.5 hours and thereafter was cooled to room temperature. The reaction mixture was poured over a column packed with silica gel and the column was eluted with benzene. Excess benzoyl peroxide passed off the column initially and on further elution with benzene, the product was collected. The eluate was evaporated under reduced pressure to provide the product, N-[α-(benzyl D-4-benzyloxyphenylacetate)]-3-benzoyl-2,2-dimethyl-4-thiazolidinecarboxamide-5α-benzoate, as an oil. The product was obtained crystalline from diethyl ether.

The above product is represented by the following structural formula

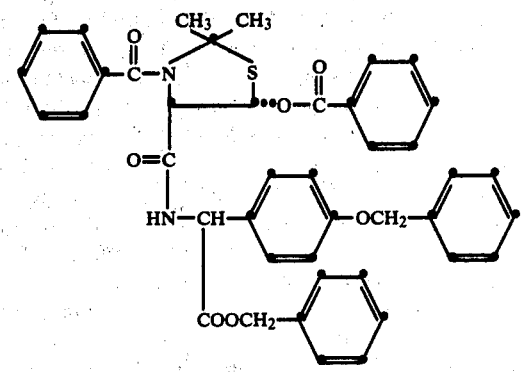

NMR (T60, CDCl$_3$): 2.16 (s, 2CH$_3$), 5.08 and 5.16 (2s, 2CH$_2$), 5.13 (s, CH), 5.54 (d, CH), 6.54 (s, CH) and 6.83–8.16 (m, aromatic H and NH) delta.

A solution of 25.5 g. (35.8 mmole) of the thiazolidine-4-carboxamide 5α-benzoate in 1 l. of dry methylene chloride was cooled to a temperature of 0° C. and hydrogen chloride was bubbled through the cold solution for about 2 hours. After this time, a thin layer chromatogram developed with benzene:ethyl acetate, 7:3, v:v, showed complete reaction. The methylene chloride was evaporated under reduced pressure providing the product as a foam. The foam was dissolved in ethyl acetate and the solution was washed with a dilute aqueous solution of sodium bicarbonate and with brine, and after washing was dried over magensium sulfate, treated with carbon, and evaporated to dryness under reduced pressure. The product, N-[α-(benzyl D-4-benzyloxyphenylacetate)]-3-benzoyl-2,2-dimethyl-5α-chloro-4-thiazolidinecarboxamide, represented by the following formula was obtained as 22.4 g. of white foam.

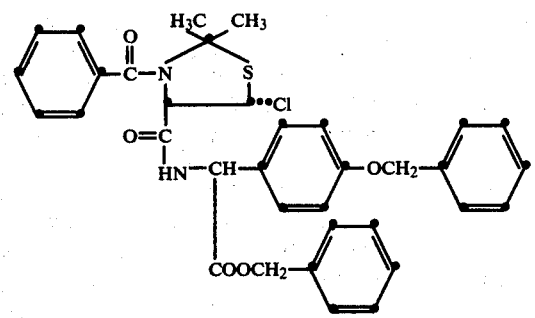

NMR (T60, CDCl$_3$): 2.12 (s, CH$_3$), 2.26 (s, CH$_3$), 5.08 and 5.16 (2s, 2CH$_2$) 5.16 (s, CH), 5.44 (d, CH), 5.83 (s, CH) and 6.08–7.5 (m, 2OH, aromatic H and NH) delta.

To a solution of 22.4 g. (35.8 mmole) of the 5α-chloro-4-thiazolidinecarboxamide in 800 ml. of methylene chloride and 200 ml. of dimethylformamide were added 1.72 g. of sodium hydride (50 percent in oil, 35.8 mmole). The reaction mixture was stirred at room temperature for approximately 50 minutes after which time TLC (benzene:ethyl acetate, 7:3) showed the reaction was complete. Two milliliters of acetic acid were added to the reaction mixture to destroy any excess sodium hydride, and the reaction mixture was poured into 5 percent hydrochloric acid. The organic phase was separated and was washed with 5 percent hydrochloric acid and with water before drying over magnesium sulfate. The dried extract was treated with carbon, filtered, and evaporated to dryness under reduced pressure. The residue was dissolved in about 30 ml. ethyl acetate. On standing, 10.1 g. (crop 1) of product crystallized. The crystals were filtered and the filtrate was treated with petroleum ether to the cloud point. On standing and with agitation, 5.5 g. (crop 2) of additional product crystallized. The second crop material was filtered and the filtrate was evaporated to dryness to yield further product as a foam. The foam was treated with a mixture of ethyl acetate and ethyl alcohol which afforded 2.2 g. of additional crystalline product (crop 3).

An analysis of the nuclear magnetic resonance spectrum (T-60) of the above crops demonstrated that crop 1 was the D isomer of the cyclized product represented by the formula shown below, crop 2 was the L isomer, while crope 3 was a mixture of the two isomers.

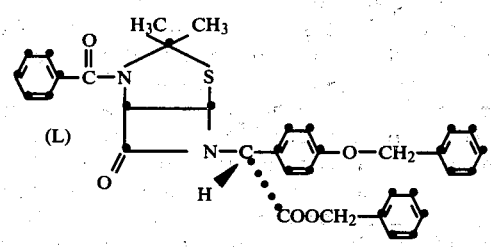

NMR (T60, CDCl$_3$): 1.70 (s, CH$_3$), 1.91 (s, CH$_3$), 5.08 and 5.16 (2s, 2CH$_2$), 5.45 (s, CH), 5.52 (m, 2CH), and 6.83–7.67 (m, 19H, aromatic H) delta.

The above thiazolidine azetidinone was also prepared with the 5α-chlorothiazolidine carboxamide and the base diazabicyclo [5.4.0]undec-5-ene(DBU) in the following manner.

To a solution of 1.01 g. (1.6 mmole) of the 5α-chloro-4-thiazolidinecarboxamide having the D-configuration in 50 ml. of methylene chloride was cooled to a temperature of about 0° C. To the cold solution was added 0.243 g. (1.6 mmole) of DBU. The reaction mixture was stirred for 2 hours at 0° C. and then was washed with 5 percent hydrochloric acid and with brine and was then dried over magnesium sulfate. The solution was evaporated to yield a crude reaction product mixture. The mixture was crystallized from benzene/petroleum ether and the crystals filtered. The infrared spectrum of the product showed an absorption peak at 1775 cm$^{-1}$ for the β-lactam carbonyl, while the nuclear magnetic resonance spectrum and circular dichromism showed the material to be optically pure.

Elemental analysis calculated for

Theory: C, 70.93; H, 5.44; N, 4.73. Found: C, 70.69; H, 5.71; N, 4.68.

A solution of 1.03 g. (1.74 mmole) of the benzyl thiazolidine azetidinone in 50 ml. of methylene chloride was cooled to a temperature of 0° C. and a solution of 352 mg. of m-chloroperbenzoic acid in methylene chloride was added to the cold solution by dropwise addition. The reaction mixture was stirred for about 30 minutes in the cold and was then washed with a dilute aqueous solution of sodium bicarbonate and with water and was then dried and treated with carbon. Evaporation under reduced pressure yielded 1.05 g. of the sulfoxide represented by the following structural formula.

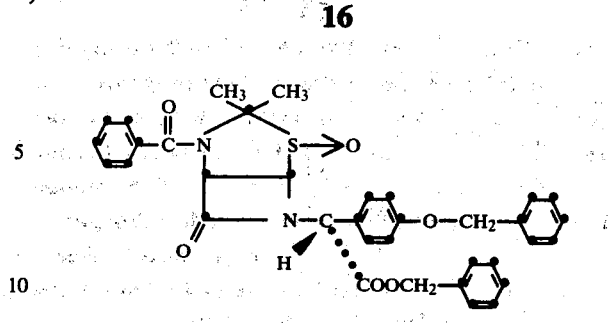

The sulfoxide was dissolved in 150 ml. of dimethyl acetamide and 150 ml. of benzene and the solution was treated with 14 drops of methanesulfonic acid and 104 drops of water. The solution was then heated at the reflux temperature for about 16 hours. The mixture was then washed with a dilute aqueous solution of sodium bicarbonate and with water, was dried, treated with carbon, filtered, and evaporated under reduced pressure. The crude reaction product mixture obtained as a residue was chromatographed on a preparative thin layer silica gel plate using benzene:ethyl acetate, 7:3, v:v for elution. There were obtained 637 mg. of product represented by the following structural formula which was yet contaminated with starting material.

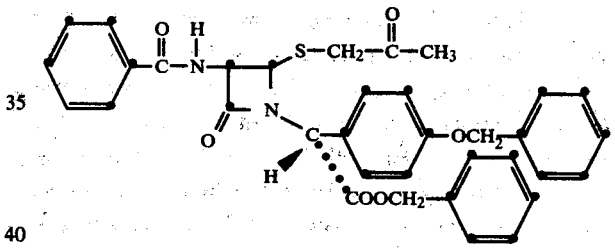

The nuclear magnetic resonance spectrum of crude product showed the correct product was present in the mixture to the extent of about 65 percent, while the remainder was the sulfoxide starting material.

The crude product was dissolved in 50 ml. of dry methylene chloride and the solution was cooled to 0° C. Sulfuryl chloride (0.62 ml., 0.77 mmole) was added to the cold solution. The solution was stirred for 30 minutes in th cold and was then washed with a dilute aqueous solution of sodium bicarbonate and with water and was dried and evaporated to dryness. The crude reaction product mixture obtained as a residue was treated with cold toluene and the sulfoxide contaminant crystallized and was filtered. The filtrate was evaporated to dryness to yield 480 mg. of the reaction product mixture. The product was purified by chromatography on a preparative silica gel thin layer plate using benzene:ethyl acetate, 7:3, v:v, for elution to yield 117 mg.

The nuclear magnetic resonance spectrum of the product although not definitive indicated a mixture containing the oxazoline of the following formula and some of the expected 4-chloroazetidin-2-one.

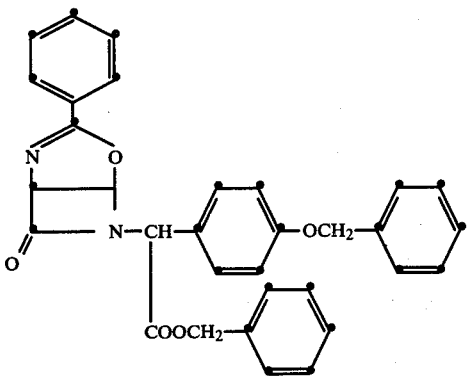

The product, 117 mg. (0.21 mmole), 0.128 ml. (0.51 mmole) of tri(n-butyl)tin hydride and 84.5 mg. (0.51 mmole) of azobisisobutyronitrile were added to 1 ml. of toluene and the solution was heated under nitrogen at a temperature of approximately 75° C. for 3.5 hours. The mixture was evaporated and the crude reaction product mixture was obtained as a residue. The residue was chromatographed on a preparative silica gel thin layer plate employing benzene:ethyl acetate, 7:3, v:v, for elution. The product 1-[α-(benzyloxycarbonyl)-4-benzyloxybenzyl]-3-benzamidoazetidinone-2, 19 mg., represented by the following structural formula was obtained.

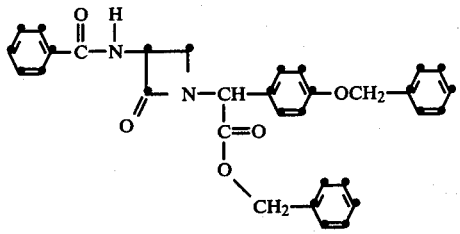

The product is dissolved in dry methylene chloride and excess phosphorus pentachloride and pyridine (an amount equimolar to the PCl₅) are added with stirring. The reaction mixture is stirred at room temperature for 30 minutes and is cooled to 5° C. in an ice bath. Excess dry methyl alcohol is added and stirring is continued in the cold for 10 minutes. Next, excess water is added and the mixture is allowed to warm to room temperature with stirring.

The mixture is diluted with water and extracted with ethyl acetate. The extract is washed with water and aqueous sodium bicarbonate and is dried. p-Toluenesulfonic acid is added to the dried extract which is cooled. On standing the p-toluenesulfonic acid salt of D-1-[α-(benzyloxycarbonyl)-4-benzyloxybenzyl]-3β-aminoazetidin-2-one precipitates and is separated by filtration.

The salt is suspended in a small volume of water layered with ethyl acetate and triethylamine is added to spring the free amine. The ethyl acetate layer is separated, washed with water and sodium bicarbonate, and is dried over magnesium sulfate.

The dried extract is filtered and excess bis-trimethylsilylacetamide is added. With stirring triethylamine and the mixed anhydride formed with methyl chloroformate and D-4-[(3-t-butyloxycarbamido)-3-(diphenylmethoxycarbonyl)propoxy]phenylglyoxylic acid are added separately to form after hydrolysis of the silyl groups the acylation product, 1-[α-(benzyloxycarbonyl)-4-benzyloxybenzyl-3β-[4-[3-(t-butyloxycarbamido)-3-(diphenylmethoxycarbonyl)propoxy]-phenylglyoxamido]azetidin-2-one.

We claim:
1. The process for preparing a 3-acylaminoazetidin-2-one of the formula

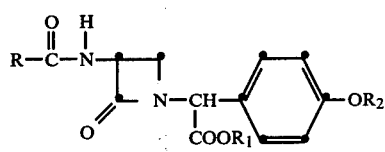

wherein
R is $C_1$–$C_3$ alkyl, phenyl, or benzyl;
$R_1$ is methyl, benzyl, 4-methoxybenzyl, diphenylmethyl, or 2,2,2-trichloroethyl; and
$R_2$ is benzyl, 4-methoxybenzyl, or diphenylmethyl;
which comprises the steps (a) reacting in an inert solvent a 3-acylthiazolidine-4-carboxamide of the formula

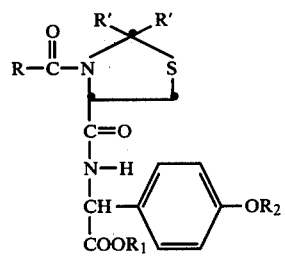

wherein R, $R_1$, and $R_2$ have the above defined meanings and both of R' are methyl or ethyl; with benzoyl peroxide to form the 5α-benzoate of the formula

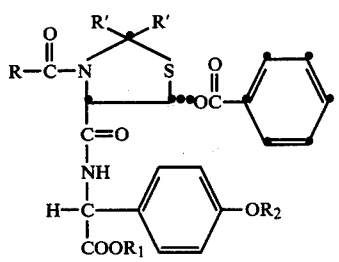

(b) reacting said benzoate in an inert solvent at a temperature between about −20° and about 5° C. with hydrogen chloride to form the 5α-chloro thiazolidine amide of the formula

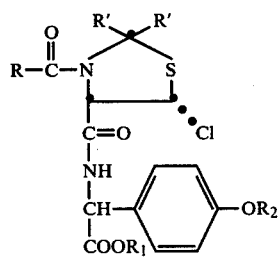

(c) cyclizing said chloro amide under anhydrous conditions in an inert solvent at a temperature between about 0° and about 30° C. with a strong base selected from the group consisting of sodium hydride and 1,5-diazabicyclo[5.4.0]-undec-5-ene to form the thiazolidine azetidin-2-one of the formula

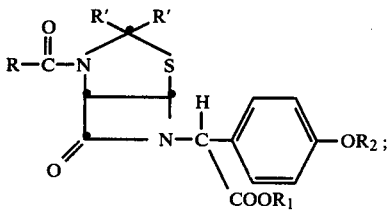

(d) oxidizing the thiazolidine azetidin-2-one with a per organic acid to the corresponding sulfoxide;

(e) heating said sulfoxide in a polar aprotic solvent in the presence of water and an acid selected from the group consisting of a lower alkylsulfonic acid, phenylsulfonic acid, p-toluenesulfonic acid or p-chlorobenzenesulfonic acid at a temperature between about 80° and about 120° C. to form a 3-acylamino-4-(oxaalkylthio)azetidin-2-one of the formula

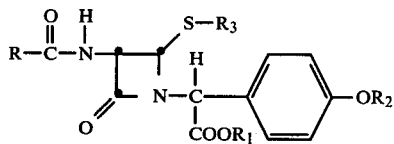

wherein R, $R_1$, and $R_2$ have the above defined meanings and $R_3$ is a 2-oxapropyl group of the formula

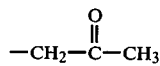

or a 2-oxapentyl group of the formula

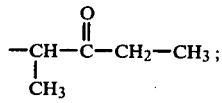

(f) reacting said 4-(oxaalkylthio)azetidin-2-one in an inert solvent with sulfuryl chloride at a temperature between about −25° C. and about 10° C.;

(g) reducing the reaction product mixture obtained in step (f) under anhydrous conditions in an inert aprotic solvent at a temperature between about 65° and about 95° C. with about a 2 molar excess of a tin hydride of the formula

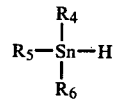

wherein $R_4$, $R_5$, and $R_6$ independently are $C_1$–$C_4$ alkyl, phenyl, or phenyl substituted by methyl or chloro, and azobisisobutyronitrile in an amount equimolar to the tin hydride; to form (h) and recovering said 3-acylaminoazetidin-2-one.

2. The process of claim 1 wherein the 3-acylamido-4-(oxaalkylthio)azetidin-2-one is reacted with sulfuryl chloride and the reaction product mixture is reduced with a tin hydride and azobisisobutyronitrile to form the 3-acylaminoazetidin-2-one.

3. The process of claim 1 where in step (c) the chloro amide is cyclized to the thiazolidine azetidin-2-one with sodium hydride.

4. The process of claim 1 where in step (e) the thiazolidine azetidin-2-one sulfoxide is heated with methanesulfonic acid.

5. The process of claim 1 where in step (g) the tin hydride is tri(n-butyl)tin hydride.

6. The process of claim 1 wherein R is phenyl, and R' is methyl.

7. The process of claim 6 wherein $R_1$ and $R_2$ are both benzyl.

8. The process of claim 6 wherein $R_1$ is methyl and $R_2$ is hydrogen.

9. The process of claim 6 wherein the 3-acylaminoazetidin-2-one has the D-configuration.

* * * * *